(12) United States Patent
Wagner

(10) Patent No.: US 11,779,345 B2
(45) Date of Patent: Oct. 10, 2023

(54) TOURNIQUET

(71) Applicant: Shane Michael Wagner, Wellington, FL (US)

(72) Inventor: Shane Michael Wagner, Wellington, FL (US)

( * ) Notice: Subject to any disclaimer, the term of this patent is extended or adjusted under 35 U.S.C. 154(b) by 209 days.

(21) Appl. No.: 17/308,955

(22) Filed: May 5, 2021

(65) Prior Publication Data

US 2021/0346035 A1 Nov. 11, 2021

Related U.S. Application Data

(60) Provisional application No. 63/021,404, filed on May 7, 2020.

(51) Int. Cl.
*A61B 17/132* (2006.01)
*A61B 17/12* (2006.01)

(52) U.S. Cl.
CPC ...... *A61B 17/1327* (2013.01); *A61B 2017/12004* (2013.01)

(58) Field of Classification Search
CPC .............. A61B 17/132; A61B 17/1322; A61B 17/1327; A61B 2017/12004
See application file for complete search history.

(56) References Cited

U.S. PATENT DOCUMENTS

| | | | |
|---|---|---|---|
| 7,051,410 B2 | 5/2006 | Simond | |
| 7,776,064 B2 | 8/2010 | Jennifer et al. | |
| D649,642 S | 11/2011 | Johnson | |
| 8,303,620 B2 | 11/2012 | Johnson et al. | |
| 8,343,182 B2 * | 1/2013 | Kirkham | A61B 17/1322 606/203 |
| D739,027 S | 9/2015 | Johnson et al. | |
| 9,380,838 B2 | 7/2016 | Iannello et al. | |
| 2005/0049630 A1 | 3/2005 | Ambach | |
| 2010/0049241 A1 | 2/2010 | Persson | |
| 2011/0307004 A1 | 12/2011 | Johnson et al. | |
| 2020/0015828 A1 | 9/2020 | Johnson et al. | |

* cited by examiner

*Primary Examiner* — Wade Miles
*Assistant Examiner* — Daniel Icet
(74) *Attorney, Agent, or Firm* — Bennet K. Langlotz; Langlotz Patent & Trademark Works, LLC

(57) ABSTRACT

Tourniquets have an elongated body having opposed first and second anchor locations, a strap having a body end connected to and extending from the first anchor location of the body, the strap having a free end, the second anchor location of the body having an adjustor buckle defining a passage receiving an intermediate portion of the strap between the body end and the free end, the adjustor buckle configured to resist movement of the strap through the passage in response to tension applied between the body and the portion of the strap extending toward the body end, and to enable movement of the strap through the passage in response to tension applied between the elongated body and a tail portion of the strap extending from the intermediate portion to the free end, the elongated body having a tightener, and the tail portion being connected to the elongated body.

10 Claims, 4 Drawing Sheets

TOURNIQUET

CROSS-REFERENCE TO RELATED APPLICATION

This application claims the benefit of U.S. Provisional Patent Application No. 63/021,404 filed on May 7, 2020, entitled "TOURNIQUET ASTRICTION APPARATUS," which is hereby incorporated by reference in its entirety for all that is taught and disclosed therein.

FIELD OF THE INVENTION

The present invention relates to medical devices used in first aid, and more particularly to a tourniquet that enables one-handed application using a single finger or improvised tool.

BACKGROUND AND SUMMARY OF THE INVENTION

A tourniquet is any type of tightening device that stops blood flow to a limb. Tourniquets are often used to stop uncontrolled hemorrhaging from trauma, as well as to stop the flow of venom from a snake bite. The tourniquet is also used in other settings, including during surgery and when drawing blood in a laboratory. Rapid application of the tourniquet above the site of injury is paramount to preventing hypovolemia shock onset within just minutes.

In emergency situations when an injured victim is alone, he or she must be able to apply the tourniquet to his or her injured body part without assistance. Tourniquet self-application is especially challenging when the victim only has the use of one hand. The tourniquet can become slick with blood, further increasing the difficulty of properly securing and tightening the tourniquet sufficiently to stop continued blood flow to the injury site.

Various prior art tourniquets suited for one-handed application exist, including the tourniquet with rotatable buckle assembly disclosed in US Patent Publication No. 2020/00158282 Johnson et al., which is hereby incorporated by reference in its entirety for all that is taught and disclosed therein. Many such tourniquets are of the windlass-type, typically including a strap threaded through a windlass handle and coupled to a tourniquet base. To tighten the tourniquet around an injured limb, the strap is threaded through a buckle, and the windlass handle is twisted, thereby causing the strap to constrict circumferentially about the limb to stop blood flow to the injured area.

Although prior art one-handed application tourniquets can be successfully applied by a victim in many circumstances, the tourniquet tends to rotate around the limb until the tourniquet is sufficiently tighten down. The victim must perform a ratcheting maneuver by pulling the strap up and down while gripping the strap firmly until the tourniquet is tight around the limb. This requirement increases the amount of time needed to securely apply the tourniquet, which delays tourniquet application where even a few seconds of delay can cause fatal blood loss. The victim's ability to grip the strap firmly can be impeded by the strap becoming slippery with blood and/or the victim becoming weak from blood loss. The victim must also have considerable clearance around the limb to perform the ratcheting motion, and it is difficult for the victim to control the final location of the windlass handle on the injured limb.

Therefore, a need exists for a new and improved tourniquet that enables one-handed application using a single finger or improvised tool. In this regard, the various embodiments of the present invention substantially fulfill at least some of these needs. In this respect, the tourniquet according to the present invention substantially departs from the conventional concepts and designs of the prior art, and in doing so provides an apparatus primarily developed for the purpose of enabling one-handed application using a single finger or improvised tool.

The present invention provides an improved tourniquet, and overcomes the above-mentioned disadvantages and drawbacks of the prior art. As such, the general purpose of the present invention, which will be described subsequently in greater detail, is to provide an improved tourniquet that has all the advantages of the prior art mentioned above.

To attain this, the preferred embodiment of the present invention essentially comprises an elongated body having opposed first and second anchor locations, a strap having a body end connected to and extending from the first anchor location of the body, the strap having a free end, the second anchor location of the body having an adjustor buckle defining a passage receiving an intermediate portion of the strap between the body end and the free end, the adjustor buckle configured to resist movement of the strap through the passage in response to tension applied between the body and the portion of the strap extending toward the body end, and to enable movement of the strap through the passage in response to tension applied between the elongated body and a tail portion of the strap extending from the intermediate portion to the free end, the elongated body having a tightener apart from the strap and adjustor buckle operable to reduce an effective length of the elongated body defined by a separation between the first and second anchor locations, and the tail portion being connected to the elongated body. There are, of course, additional features of the invention that will be described hereinafter and which will form the subject matter of the claims attached.

There has thus been outlined, rather broadly, the more important features of the invention in order that the detailed description thereof that follows may be better understood and in order that the present contribution to the art may be better appreciated.

BRIEF DESCRIPTION OF THE DRAWINGS

The same reference numerals refer to the same parts throughout the various figures.

DESCRIPTION OF THE CURRENT EMBODIMENT

Figure 1:
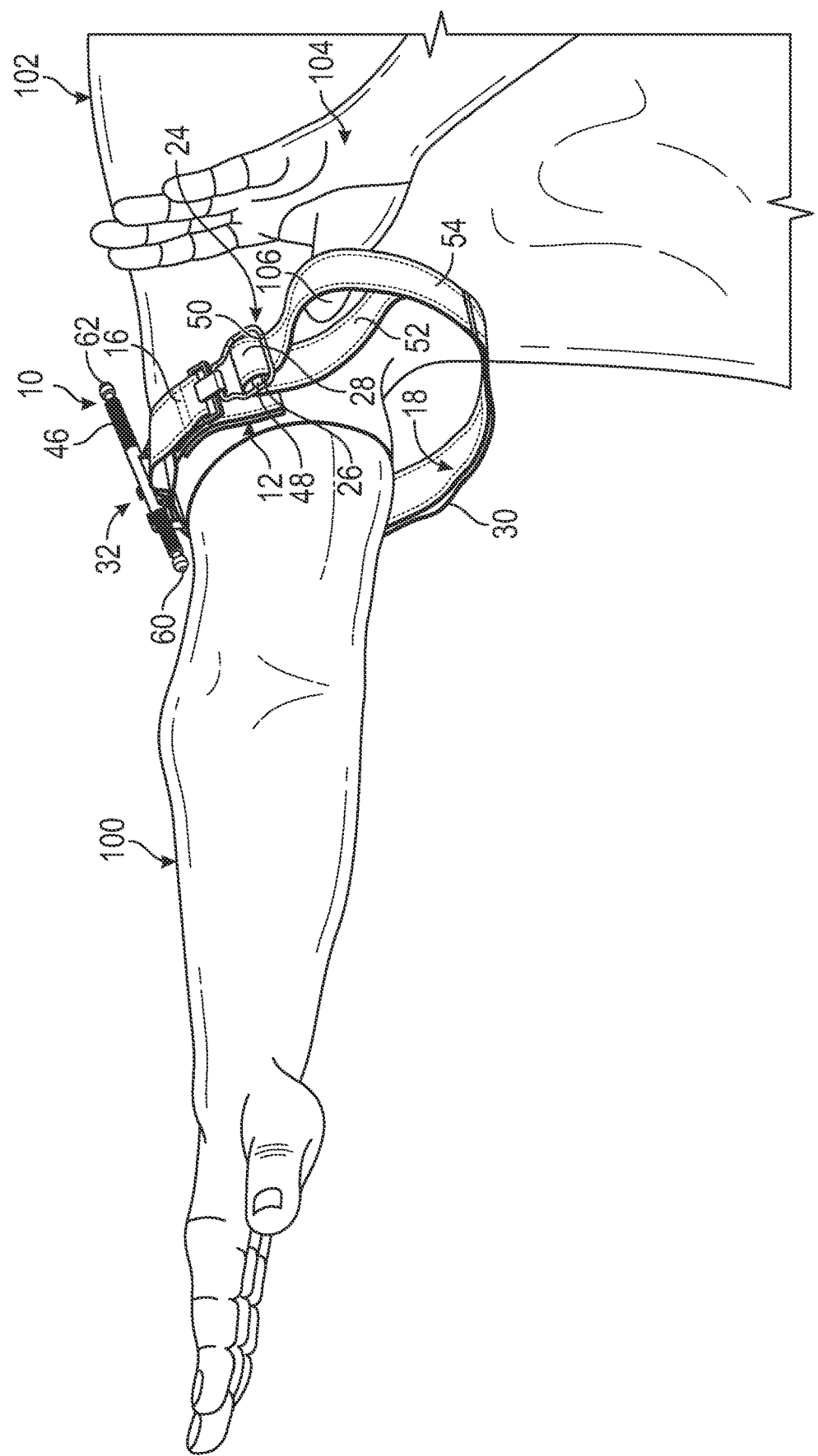
FIG. 1 is a plan view of the current embodiment of a tourniquet constructed in accordance with the principles of the present invention in use being applied one-handed to a victim's arm.

An embodiment of the tourniquet of the present invention is shown and generally designated by the reference numeral 10.

Figure 2:
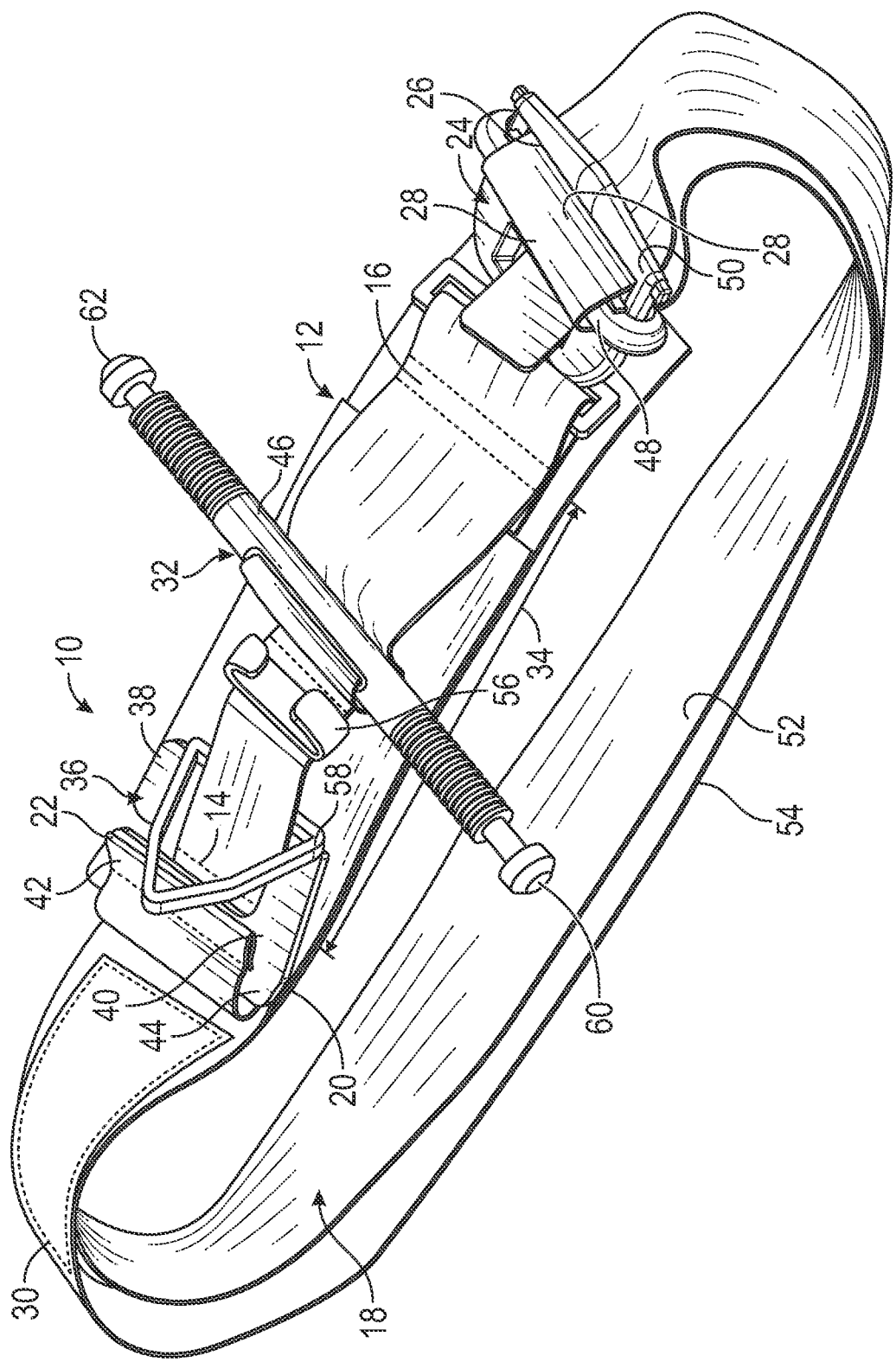
FIG. 2 is a top perspective view of the tourniquet of FIG. 1 detached from the victim's arm.

FIGS. 1 & 2 illustrate the improved tourniquet 10 of the present invention. More particularly, FIG. 1 shows the tourniquet in use being applied one-handed to an arm 100 of a victim 102. The tourniquet has an elongated body 12 having opposed first and second anchor locations 14, 16, a strap 18 having a body end 20 connected to and extending from the first anchor location of the body, the strap having a free end 22. The second anchor location of the body has an adjustor buckle 24 defining a passage 26 receiving an intermediate portion 28 of the strap between the body end and the free end. The adjustor buckle has a first bar 48 and second bar 50 spaced apart to define the passage. The intermediate portion of the strap wraps about the first bar and extends on one side of the second bar. In the current embodiment, the adjustor buckle is configured to resist movement of the strap through the passage in response to tension applied between the elongated body and the portion of the strap extending toward the body end, and to enable movement of the strap through the passage in response to tension applied between the elongated body and a tail portion 30 of the strap extending from the intermediate portion to the free end. The elongated body has a tightener 32 apart from the strap and adjustor buckle operable to reduce an effective length of the elongated body defined by a separation 34 between the first and second anchor locations.

Figure 3:
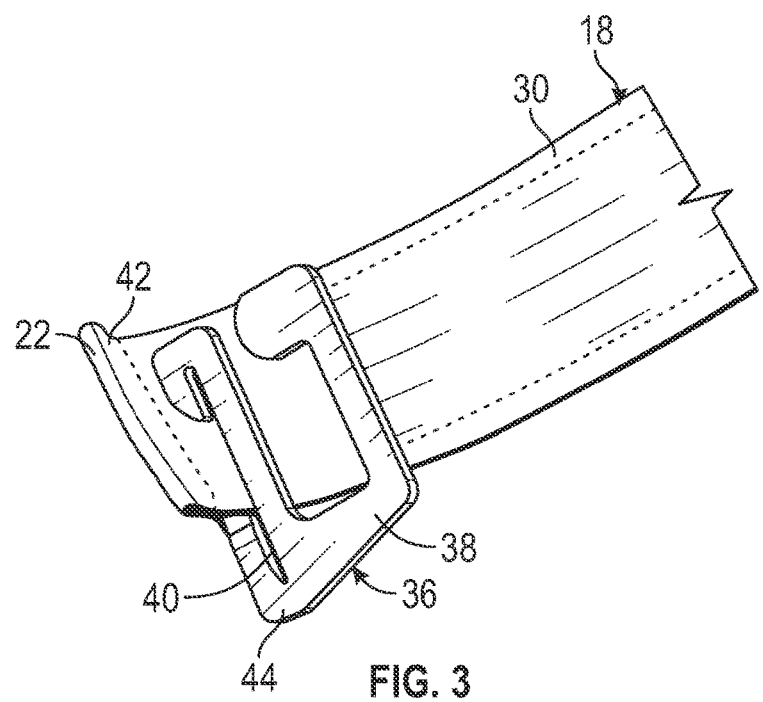
FIG. 3 is a top perspective view of the hook facility and the tail portion of the strap of FIG. 1 showing the hook facility in the process of being connected to the tail portion of the strap.

In the current embodiment, the tail portion 30 of the strap 18 is removably connected to the elongated body 12 at the first anchor location 14 by the free end 22. A hook facility 36 is connected to the tail portion and has a hook element 38 configured to engage a portion of the elongated body, which is the first anchor location in the current embodiment. The hook facility includes a hook passage portion 40 that receives a portion 42 of the tail portion, which is a small fold of sewn material that creates a pathway at the free end of the strap. FIG. 3 illustrates the hook facility in the process of being connected to the portion 42 of the tail portion. The hook facility also includes a hook 44 configured with a limited strength characteristic relative to the hook passage portion to fail under tension such that the hook passage portion remains attached to the tail portion after hook failure.

The tightener 32 includes a torsion element 46 configured to be twisted to generate the reduction of effective length of the elongated body 12. The tail portion 30 of the strap 18 is releasably connected to the torsion element by the hook facility 36. The strap, elongated body, and tightener are configured to withstand a selected tension force operable to generate a desired constrictive effect, and the hook facility is configured with a limited dimension to fail under a breakaway tension force less than the selected tension force. In the current embodiment, the selected tension force is greater than the breakaway tension force by at least a factor of 75 lbs. (333.54 N) of force.

When the hook facility 36 releasably connects the tail portion 30 of the strap 18 to the first anchor location 14 on the elongated body 12, the strap forms an inner loop 52 and an outer loop 54. To apply the tourniquet 10, the victim positions the tourniquet on the desired limb above the wound causing massive bleeding. The victim then exerts force on the outer loop as is shown in FIG. 1 using a hand 104, one or more fingers 106, or an improvised tool (not shown) to pull the intermediate portion 28 of the strap through the passage 26 of the adjustor buckle 24 to tighten the inner loop about the victim's limb (arm 100 is shown in FIG. 1). The victim can reposition the tourniquet if needed to optimize the location of the tightener 32 before completing the initial tightening of the inner loop. Elimination of the ratcheting motion associated with prior art tourniquets ensures the location of the tightener on the victim's limb does not change because of tourniquet rotation. Subsequently, the victim twists the torsion element 46 to reduce the effective length of the elongated body, thereby tightening the tourniquet further to stop the flow of blood in the limb past the tourniquet. When the bleeding has stopped, the victim traps the torsion element in a C-clip 56 attached to the elongated body and locks the torsion element in the final position by placing a triangular lock 58 over one of the opposing ends 60, 62 of the torsion element.

Figure 4:
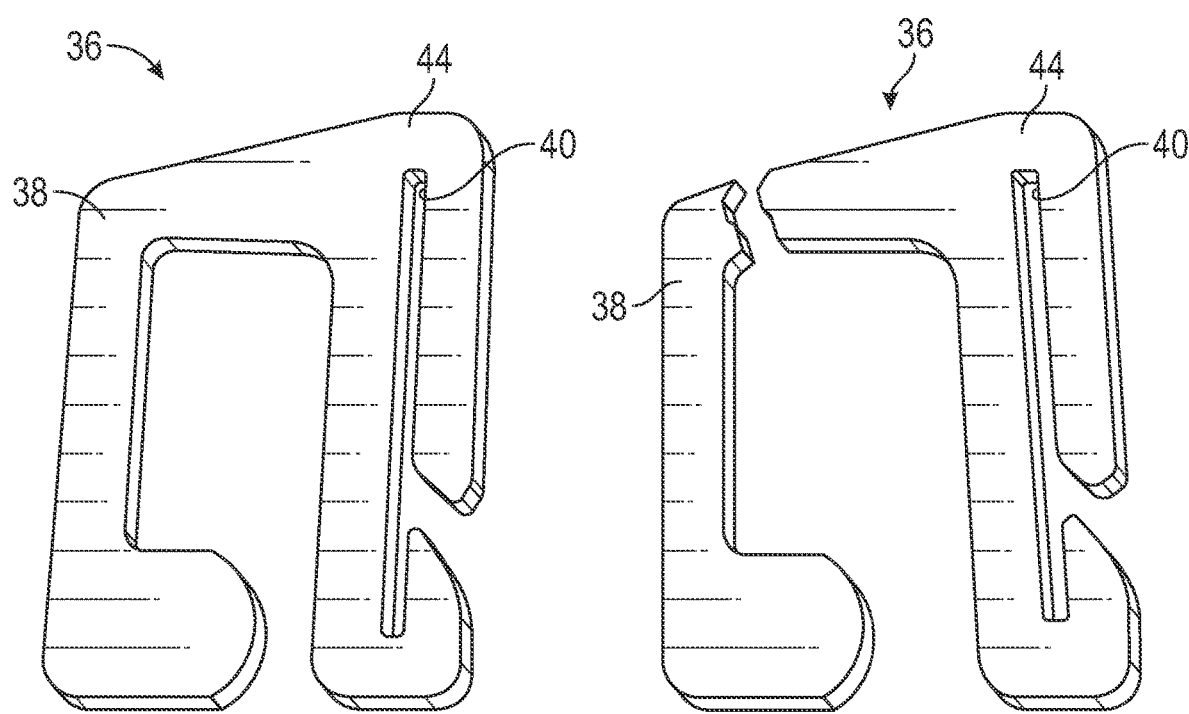
FIG. 4 is a top view of the hook facility of FIG. 1 showing the hook facility in the intact condition and the failed condition.

If the inner loop 52 and outer loop 54 of the strap 18 are too small to fit over the injured limb, such as a thigh, or apparel, such as a boot, the victim 102 can easily eliminate the outer loop and enlarge the inner loop by applying a breakaway tension force to the hook facility sufficient to cause the hook facility to fail, thereby disengaging the tail portion 30 of the strap 18 from the elongated body 12. The disengagement enables more of the intermediate portion 28 of the strap to be pulled through the passage 26 in the adjustor buckle 24 to enlarge the inner loop than is otherwise possible when the tail portion of the strap is connected to the elongated body to form the outer loop. FIG. 4 illustrates the hook facility in the intact and failed conditions. The deliberate inclusion of a limited strength characteristic in the hook 44 enables the victim to quickly break the hook facility instead of having to devote precious time to disconnecting the hook facility from either the tail portion of the strap or the first anchor location 14 on the elongated body. Once the tail portion of the strap has been disconnected from the first anchor location on the elongated body and the tourniquet has been applied on the desired limb above the wound causing massive bleeding, the victim grips the strap and tightens the inner loop using the conventional ratcheting maneuver associated with prior art tourniquets.

Figure 5:
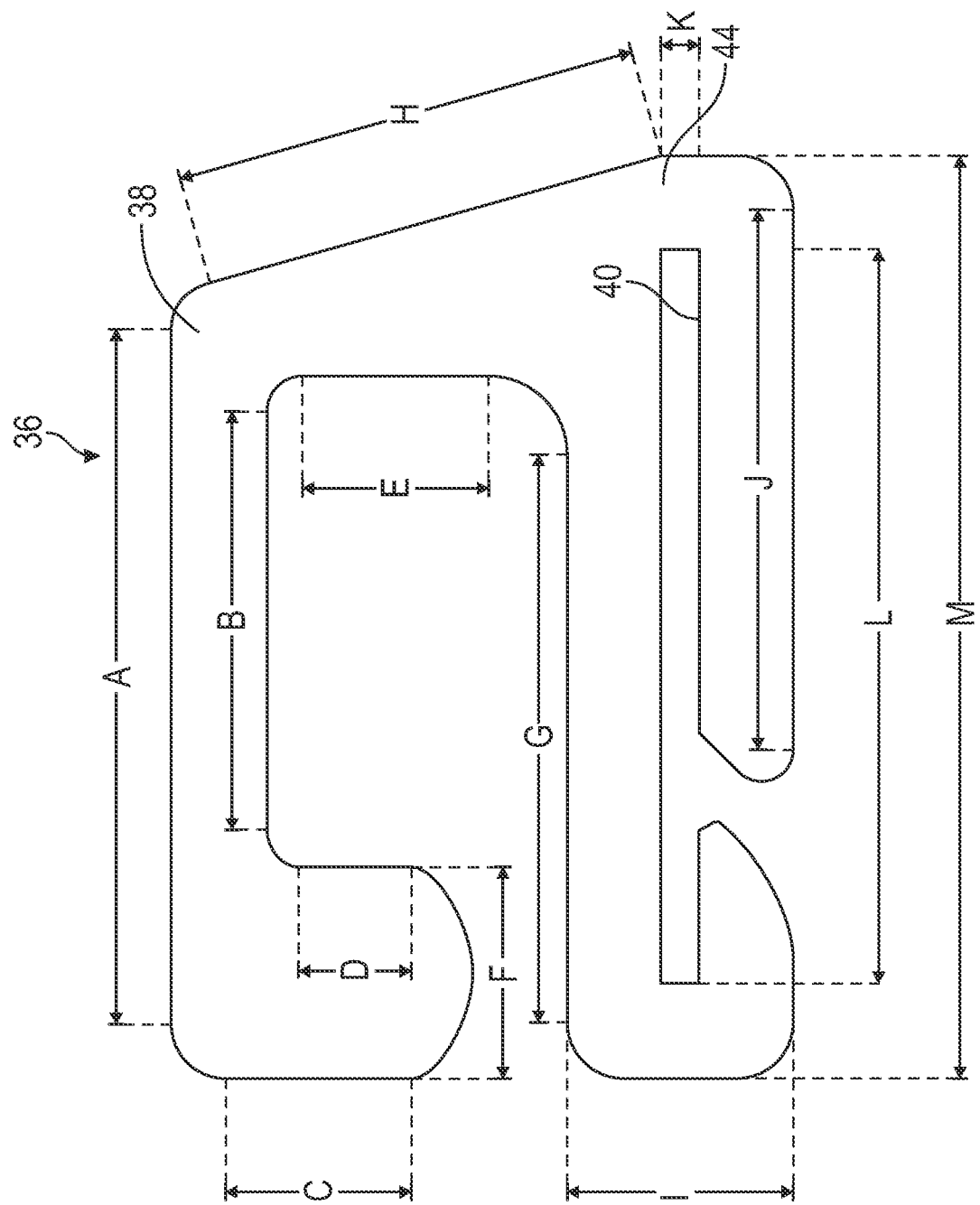
FIG. 5 is a top enlarged view of the hook facility of FIG. 1 showing the hook facility in the intact condition.

FIG. 5 illustrates the improved hook facility 36 of the present invention. More particularly, the hook facility has the following dimensions: portion A=36.541729 mm, portion B=22.522098 mm, portion C=10.000000 millimeters, portion D=6.261124 mm, portion E=10.050189 mm, portion F=1.250000 mm, portion G=10.039137 mm, portion H=24.947915 mm, portion I=12.000000 mm, portion J=28.471825 mm, portion K=2.000000 millimeters, portion L=39.000000 mm, and portion M=49.000000 mm.

While a current embodiment of a tourniquet has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly, and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A tourniquet comprising:
an elongated body having opposed first and second anchor locations;
a strap having a body end connected to and extending from the first anchor location of the body;
the strap having a free end;
the second anchor location of the body having an adjustor buckle defining a passage receiving an intermediate portion of the strap between the body end and the free end;
the adjustor buckle configured to resist movement of the strap through the passage in response to tension applied between the elongated body and the portion of the strap extending toward the body end, and to enable movement of the strap through the passage in response to tension applied between the elongated body and a tail portion of the strap extending from the intermediate portion to the free end;
the tail portion being an elongated portion having opposed first and second end portions spaced apart from each other, the first end portion being connected proximate the buckle, and the second end portion being apart from the buckle;
the elongated body having a tightener apart from the strap and adjustor buckle operable to reduce an effective length of the elongated body defined by a separation between the first and second anchor locations; and
the second end portion of the tail portion being connected to the elongated body at a location apart from the buckle.

2. The tourniquet of claim 1 wherein the free end of the strap is connected to the elongated body.

3. The tourniquet of claim 1 wherein the tail portion is connected to the first anchor location.

4. The tourniquet of claim 1 wherein the tail portion is removably connected to the elongated body.

5. The tourniquet of claim 1 wherein the tightener includes a torsion element configured to be twisted to generate the reduction of effective length, and wherein the tail portion is connected to the torsion element.

6. The tourniquet of claim 1 including a hook facility connected to the tail portion and having a hook element configured to engage a portion of the elongated body.

7. The tourniquet of claim 1 wherein the adjustor buckle has a first bar and second bar spaced apart to define the passage, the intermediate portion of the strap wrapping about the first bar and extending on one side of the second bar.

8. A tourniquet comprising:
an elongated body having opposed first and second anchor locations;
a strap having a body end connected to and extending from the first anchor location of the body;
the strap having a free end;
the second anchor location of the body having an adjustor buckle defining a passage receiving an intermediate portion of the strap between the body end and the free end;
the adjustor buckle configured to resist movement of the strap through the passage in response to tension applied between the elongated body and the portion of the strap extending toward the body end, and to enable movement of the strap through the passage in response to tension applied between the elongated body and a tail portion of the strap extending from the intermediate portion to the free end;
the elongated body having a tightener apart from the strap and adjustor buckle operable to reduce an effective length of the elongated body defined by a separation between the first and second anchor locations; and
the tail portion being connected to the elongated body;
including a hook facility connected to the tail portion and having a hook element configured to engage a portion of the elongated body;
wherein the strap, elongated body, and tightener are configured to withstand a selected tension force operable to generate a desired constrictive effect, and the hook facility is configured with a limited dimension to fail under a breakaway tension force less than the selected tension force.

9. The tourniquet of claim 8 wherein the selected tension force is greater than the breakaway tension force by at least a factor of 75 lbs. of force.

10. A tourniquet comprising:
an elongated body having opposed first and second anchor locations;
a strap having a body end connected to and extending from the first anchor location of the body;
the strap having a free end;
the second anchor location of the body having an adjustor buckle defining a passage receiving an intermediate portion of the strap between the body end and the free end;
the adjustor buckle configured to resist movement of the strap through the passage in response to tension applied between the elongated body and the portion of the strap extending toward the body end, and to enable movement of the strap through the passage in response to tension applied between the elongated body and a tail portion of the strap extending from the intermediate portion to the free end;
the elongated body having a tightener apart from the strap and adjustor buckle operable to reduce an effective length of the elongated body defined by a separation between the first and second anchor locations; and
the tail portion being connected to the elongated body;
including a hook facility connected to the tail portion and having a hook element configured to engage a portion of the elongated body;
wherein the hook facility includes a hook passage portion receiving a portion of the tail portion, and a hook configured with a limited strength characteristic relative to the hook passage portion to fail under tension such that the hook passage portion remains attached to the tail portion after hook failure.

* * * * *